US007514259B2

(12) United States Patent
Young et al.

(10) Patent No.: US 7,514,259 B2
(45) Date of Patent: Apr. 7, 2009

(54) ISOLATION AND TRANSPLANTATION OF RETINAL STEM CELLS

(75) Inventors: Michael J. Young, Gloucester, MA (US); Henry J. Klassen, Pasadena, CA (US); Marie A. Shatos, Athol, MA (US); Keiko Mizumoto, Higashi (JP)

(73) Assignee: Schepens Eye Research Institute, Boston, MA (US)

( * ) Notice: Subject to any disclaimer, the term of this patent is extended or adjusted under 35 U.S.C. 154(b) by 267 days.

(21) Appl. No.: 10/203,105

(22) PCT Filed: Feb. 12, 2001

(86) PCT No.: PCT/US01/04419

§ 371 (c)(1), (2), (4) Date: Aug. 6, 2002

(87) PCT Pub. No.: WO01/58460

PCT Pub. Date: Aug. 16, 2001

(65) Prior Publication Data

US 2003/0207450 A1    Nov. 6, 2003

Related U.S. Application Data

(60) Provisional application No. 60/181,723, filed on Feb. 11, 2000.

(51) Int. Cl.
*C12N 5/08* (2006.01)
*C12N 5/06* (2006.01)
*C12N 5/10* (2006.01)
*C12N 5/00* (2006.01)
*C12N 5/02* (2006.01)
*A01N 63/00* (2006.01)
*A01N 65/00* (2006.01)

(52) U.S. Cl. ................... 435/366; 435/363; 435/325; 424/93.7

(58) Field of Classification Search ............... 435/325; 800/8
See application file for complete search history.

(56) References Cited

U.S. PATENT DOCUMENTS

| 5,359,046 A | 10/1994 | Capon et al. ............. 536/23.4 |
| 5,654,183 A | 8/1997 | Anderson et al. ......... 435/172.3 |
| 5,672,499 A | 9/1997 | Anderson et al. ......... 435/240.4 |
| 5,693,482 A | 12/1997 | Anderson et al. ............. 435/29 |
| 5,750,376 A | 5/1998 | Weiss et al. ............ 435/69.52 |
| 5,753,506 A | 5/1998 | Johe ........................... 435/377 |
| 5,776,747 A | 7/1998 | Schinstine et al. .......... 435/177 |
| 5,795,790 A | 8/1998 | Schinstine et al. .......... 435/382 |
| 5,824,489 A | 10/1998 | Anderson et al. ........... 435/7.21 |
| 5,833,979 A | 11/1998 | Schinstine et al. ......... 424/93.21 |
| 5,840,576 A | 11/1998 | Schinstine et al. .......... 435/325 |
| 5,843,431 A | 12/1998 | Schinstine et al. ......... 424/93.21 |
| 5,849,553 A | 12/1998 | Anderson et al. ......... 435/172.3 |
| 5,851,832 A | 12/1998 | Weiss et al. .................. 435/368 |
| 5,853,717 A | 12/1998 | Schinstine et al. ......... 424/93.21 |
| 5,858,747 A | 1/1999 | Schinstine et al. .......... 435/182 |
| 5,861,283 A | 1/1999 | Levitt et al. ................ 435/69.4 |
| 5,928,947 A | 7/1999 | Anderson et al. ........... 435/455 |
| 5,935,849 A | 8/1999 | Schinstine et al. .......... 435/325 |
| 5,958,767 A | 9/1999 | Snyder et al. ............... 435/368 |
| 5,968,829 A | 10/1999 | Carpenter .................... 435/467 |
| 5,980,885 A | 11/1999 | Weiss et al. ............... 424/93.21 |
| 5,981,165 A | 11/1999 | Weiss et al. .................... 435/4 |
| 6,001,654 A | 12/1999 | Anderson et al. ............ 435/377 |
| 6,033,906 A | 3/2000 | Anderson .................... 435/325 |
| 6,071,889 A | 6/2000 | Weiss et al. .................... 514/44 |
| 6,093,531 A | 7/2000 | Bjornson et al. ............. 435/1.1 |
| 6,103,530 A | 8/2000 | Carpenter .................... 435/405 |
| 6,117,675 A | 9/2000 | van der Kooy et al. ...... 435/354 |
| 6,165,783 A | 12/2000 | Weiss et al. ................. 435/325 |
| 6,171,610 B1 | 1/2001 | Vacanti et al. ............... 424/426 |
| 6,184,035 B1 | 2/2001 | Csete et al. .................. 435/377 |

FOREIGN PATENT DOCUMENTS

| WO | WO 94/09119 | 4/1994 |
| WO | WO 94/10292 | 5/1994 |
| WO | WO 94/16718 | 8/1994 |
| WO | WO 95/13364 | 5/1995 |
| WO | WO 96/09543 | 3/1996 |
| WO | WO 96/15226 | 5/1996 |
| WO | WO 97/35605 | 10/1997 |
| WO | WO 99/21966 | 5/1999 |
| WO | WO 99/55838 | 11/1999 |
| WO | WO 00/47718 | 8/2000 |

OTHER PUBLICATIONS

McFarlane et al. (1998, Development, 125: 3967-3975).*
Ross, et al. 1995, Histology, A Text and Atlas, 3rd edition, Williams and Wilkins: Baltimore, pp. 749-756.*

(Continued)

*Primary Examiner*—Joanne Hama
(74) *Attorney, Agent, or Firm*—Rissman Jobse Hendricks & Oliverio LLP

(57) ABSTRACT

The present invention relates to the isolation, in vitro propagation, and transplantation and integration of non-pigmented retinal stem cells derived from the neuroretina of the eye, ex vivo and in vivo.

7 Claims, 14 Drawing Sheets

OTHER PUBLICATIONS

Whiteley, et al., 1996, Experimental Neurology, 140: 100-104.*
DiLoreto et al. 1996, Experimental Neurology, 140: 37-42.*
Zhang and Bok 1998, Investigative Opthalmology and Visual Science, 39: 1021-1027.*
Haurta, et al., (IVOS, Mar. 15, 1999, vol. 40, No. 4. pp. S728).*
Pera et al., 2000, Journal of Cell Science, 113:5-10.*
Ostenfeld et al., 2002, Developmental Brain Research, 134: 43-55.*
Klassen et al., 2004, IOVS, 45: 4167-4173.*
Claes, et al., 2004, IOVS, 45: 2039-2048.*
Zahir et al., 2005, Stem Cells, 23: 424-432.*
Minanov et al., 1997, Transplantation, 64: 182-186.*
van Hoof et al., 2006, Molecular and Cellular Proteomics, 5: 1261-1273.*
Osborne et al., 1999, Survey of Opthalmology, 43: S102-S128.*
Nagashima et al., 1981, Acta Neuropathol., 53: 333-336.*
Lu et al., 2002, Brain Research, 943, 292-300.*
Stern et al., 2006, Retinal Repair by Stem Cell Transplantation, Springer: London, pp. 259-280.*
Bjornson, C.R.R. et al., "Turning Brain into Blood: A Hematopoietic Fate Adopted by Adult Neural Stem Cells in Vivo.", Science, 283:534-537 (Jan. 1999).
Gage, F.H. et al., "Survival and Differentiation of Adult Neuronal Progenitor Cells Transplanted to the Adult Brain", Proc. Natl. Acad. Sci. USA 92:11879-11883 (Dec. 1995).
Flax, J.D. et al., "Engraftable Human Neural Stem Cells Respond to Developmental Cues, Replace Neurons, and Express Foreign Genes", Nature Biotech., 16:1033-1039 1996.
Eriksson, P.S. et al., "Neurogenesis in the Adult Human Hippocampus", Nature Med., 4(11):1207, 1313-1317 (Nov. 1998).
Palmer, T.D. et al., "The Adult Rat Hippocampus Contains Primordial Neural Stem Cells", Molecular and Cellular Neurosci., 8:389-404 (1997).
Shihabuddin, L.S. et al., "FGF-2 is Sufficient to Isolate Progenitors Found in the Adult Mammalian Spinal Cord", Experimental Neurology, 148:577-586 (1997).
Suhonen, J.O. et al., "Differentiation of Adult Hippocampus-Derived Progenitors into Olfactory Neurons in Vivo", Nature, 383:624-627 (Oct. 1996).
Shihabuddin, L.S. et al., "The Adult CNS Retains the Potential to Direct Region-Specific Differentiation of a Transplanted Neuronal Precursor Cell Line", J. of Neursci., 15(10):6666-6678 (Oct. 1995).
Perron et al., "Retinal Stem Cells in Vertebrates", Bioessays, vol. 22, No. 8, pp. 685-688 Aug. 2000.
Ahmad et al., "Identification of Neural Progenitors in the Adult Mammalian Eye", Biochemical and Biophysical Research Communications, vol. 270, No. 2, pp. 517-521, Apr. 2000.
Ikawa et al., "Green Fluorescent Protein as a Marker in Transgenic Mice", Development Growth and Differentiation, Japanese Society of Developmental Biologists, vol. 37, No. 1, pp. 455-459, Aug. 1995.
Ahmad et al., "Progenitor Cell and Retinal Development: Before and After", Paper Presentation, JOVS vol. 41, No. 4, Abstracts of Paper Presentations, Mar. 2000.

* cited by examiner

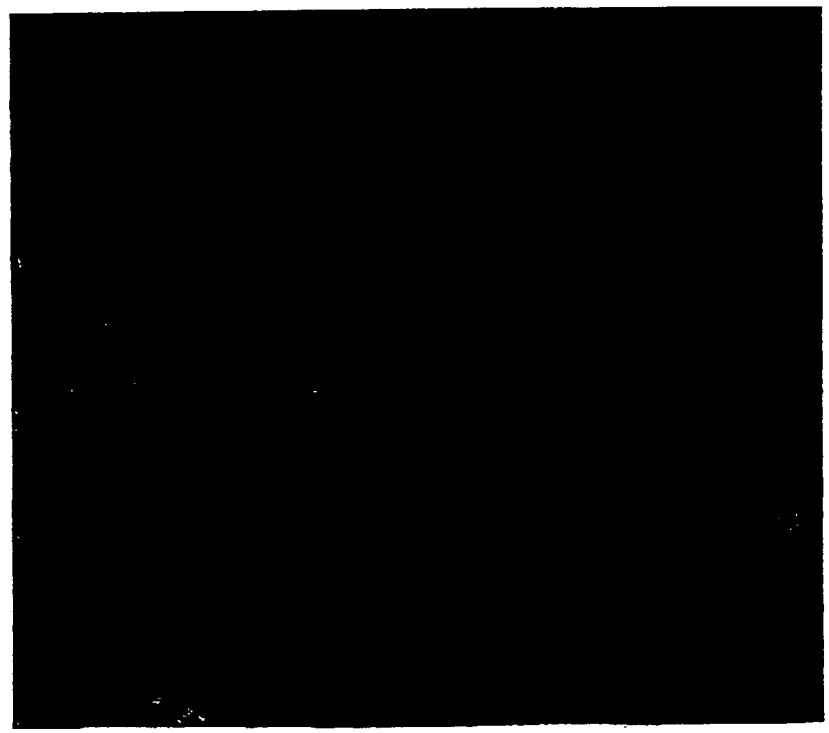
FIG. 2B
FIG. 2A

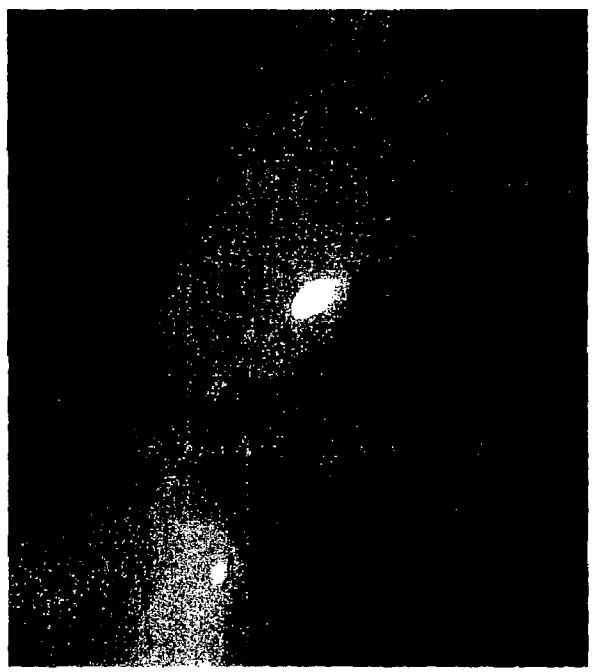 
*FIG. 5A*  *FIG. 5B*

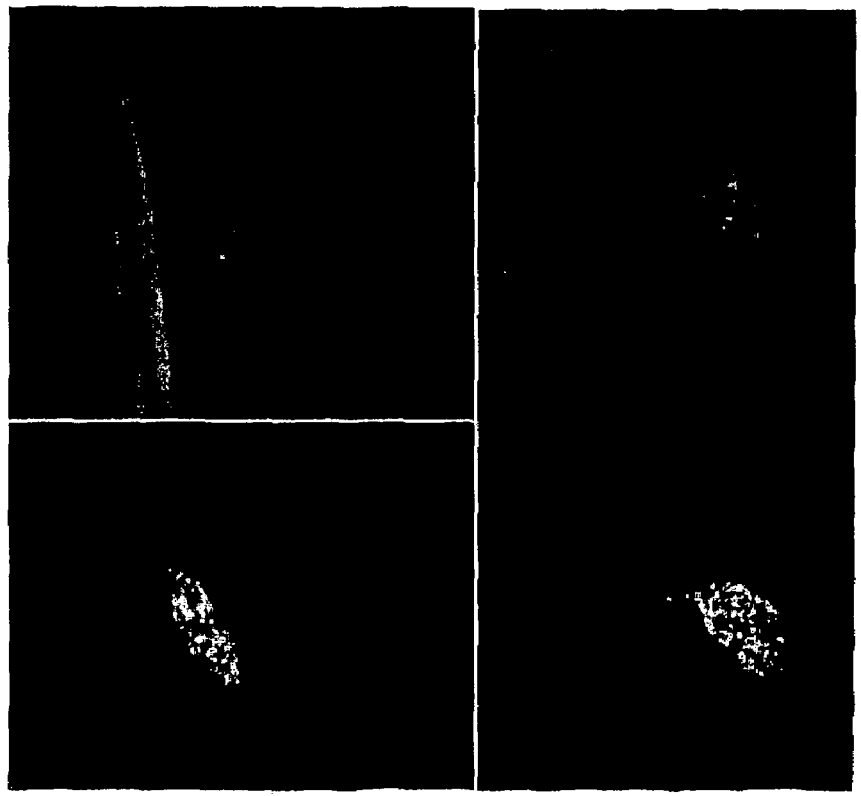

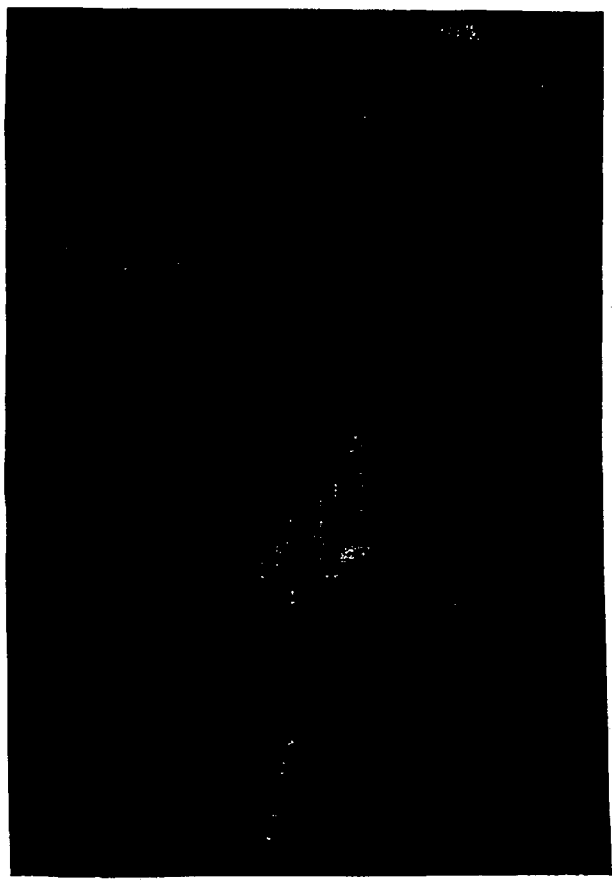
FIG. 9A
FIG. 9B
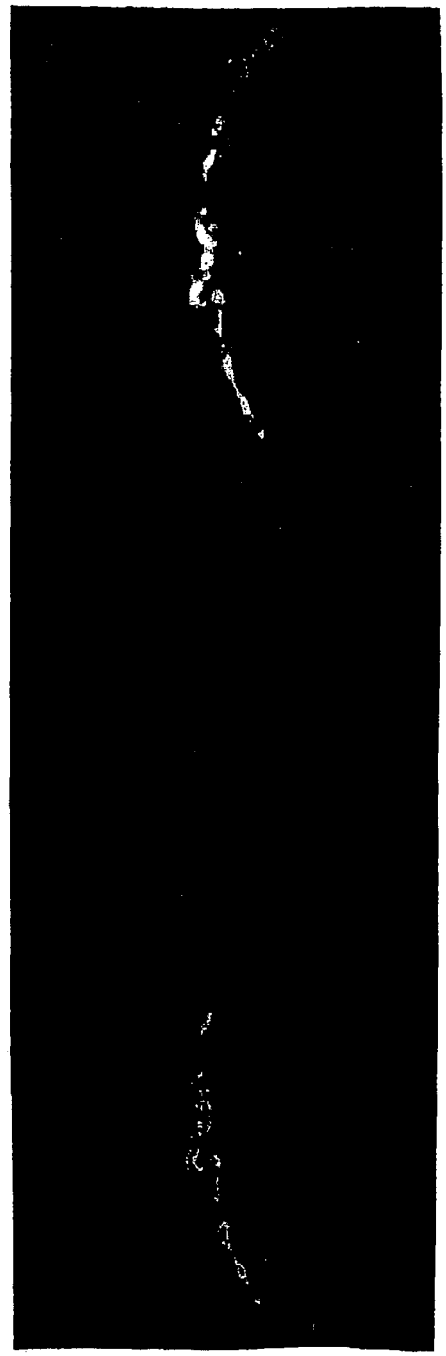
FIG. 10A
FIG. 10B
FIG. 10C

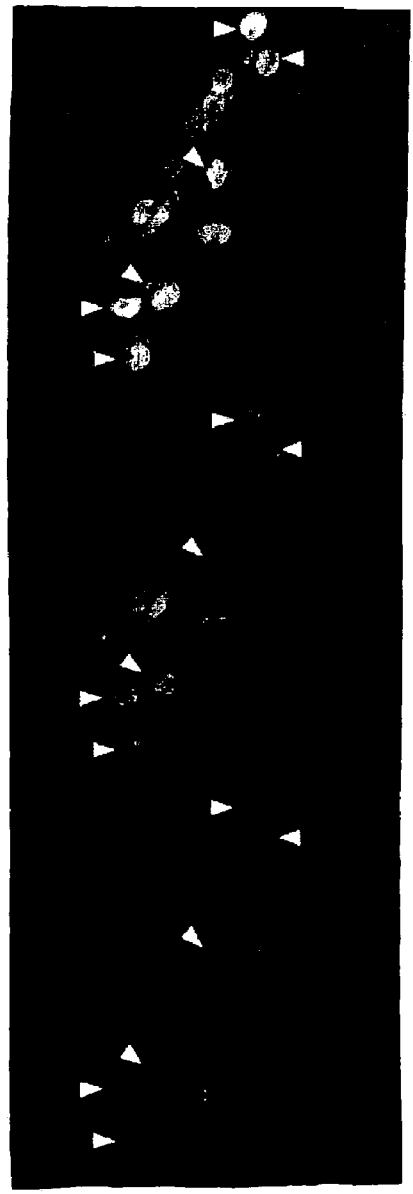

ISOLATION AND TRANSPLANTATION OF RETINAL STEM CELLS

CROSS REFERENCE TO RELATED APPLICATIONS

This application claims the benefit of U.S. Provisional Patent Application No. 60/181,723, filed on Feb. 11, 2000, the whole of which is hereby incorporated by reference.

BACKGROUND

As part of the central nervous system, both developmentally and phenotypically, the retina shares the recalcitrance of brain and spinal cord with respect to functional repair. This is unfortunate in that, among heritable conditions alone, there are over 100 examples of diseases involving the loss of retinal neurons. One strategy for replacing these cells has been to transplant retinal tissue from healthy donors to the retina of the diseased host. While the results of such studies have been encouraging in terms of graft survival, the problem of integration between graft and host has proved daunting.

Studies of retinal development have been possible, using fetal human retinal cell cultures (e.g., Kelley et al.[10]). However, such cultured cells are not stem or progenitor cells as they lack the multipotency characteristic of ture stem cells. The recent isolation and amplification of multipotent stem cells (variously referred to as progenitor cells, immature cells, undifferentiated cells, or proliferative cells), in a laboratory setting[1,2] has enlivened the fields of mammalian development and transplantation. Some have shown that examples of these proliferative, stem or progenitor cells, present in the adult rodent hippocampus, can be isolated, cultured and transplanted into various sites within the central nervous system (CNS), where they can differentiate into neurons or glial cells. It has also been shown that transplanted adult hippocampal progenitor cells are able to migrate into, and differentiate within, the mature dystrophic retina. However, the isolation of true stem cells from the neuroretina, particularly ones able to differentiate into functional photoreceptor cells both in vitro and in vivo, has proven elusive.

Recently, van der Kooy et al., in U.S. Pat. No. 6,117,675 (September 2000), have described a putative "retinal stem cell" derived from the ciliary marginal zone pigment epithelial layer, which cell is not found in neuroretina, is pigmented, is nestin-negative, and can proliferate and be passed in the absence of any growth factor. Such pigmentation, nestin negativity, and non-reliance on growth factors are unusual for mammalian stem cells. As well, van der Kooy et al. provide no evidence of the ability of their putative retinal stem cells to integrate into a host retina and to differentiate into functional mature cells, in vivo.

Additionally, the very plasticity that makes stem cells so interesting biologically, makes them difficult to track as they integrate into host tissues.

Therefore, there remains a need for multipotent, neuroretinal stem cells that can be amplified ex vivo and that readily differentiate into photoreceptor cells following transplantation to the eye, which is met by the present invention. The present invention also provides a method of tracking these cells when introduced into a host organism.

SUMMARY OF THE INVENTION

We report here the first successful isolation of viable stem cells derived explicitly from neural retinal tissue (sometimes also referred to as "neuroretina", as opposed to the underlying non-neuronal retinal pigment epithelium), particularly from post-natal tissue. These neuroretina-derived retinal stem cells (also abbreviated herein as "NRSC" or "RSC") are true stem cells in that they are capable of self-renewal, and of multipotent and retina-specific differentiation. These cells have been isolated from both murine and adult human retinal tissue. Unlike any previously described stem or progenitor cells, these cells have been shown to be capable of differentiating into photoreceptors in vivo, when transplanted to the mature diseased eye. Thus, these cells are true retinal stem cells.

Described here for the first time, viable stem cells have now been isolated from both immature and adult murine neuroretinal tissue. For the immature donor, there appears to be a window of opportunity in the late embryonic to early post natal time period (i.e., between about 5 days pre-natal and 1-2 days post natal) within which stem cells can be obtained from the neuroretina.

Human neuroretina-derived stem cells have also been isolated from adult donors. Surprisingly, we have found that neuroretina-derived retinal stem cells can be isolated from retinal tissue obtained from aged donors (including 70 years of age or older).

A number of important points relate specifically to the present invention's neuroretinal stem cells. The retinal stem cells of the present invention are specifically derived from the neural retina and not from pigmented cells of the retinal pigment epithelium, the ciliary body, or the iris. The non-pigmented stem cells of this invention thus stand in direct contrast to the pigmented cells described as "retinal stem cells" by van der Kooy et al., U.S. Pat. No. 6,117,675. The van der Kooy et al. patent specifically states that their pigmented cells cannot be obtained from the neuroretina, whereas the current invention uses exclusively non-pigmented, neural retinal tissue for derivation of the stem cells described.

Also in contrast to the "retinal stem cells" of van der Kooy et al., the NRSCs of the invention do not proliferate in the absence of growth factors. They must be induced to proliferate by the addition of serum and/or exogenous growth factors to their culture medium. Because the NRSCs of the invention proliferate only under the control of growth factors, they are readily distinguished from cells that proliferate in a factor-autonomous fashion, particularly those originating from ocular tumors such as medulloepitheliomas that are well-known to recapitulate ocular (including retinal) cell types.

Cultures of the human NRSCs of the invention also benefit from the addition of conditioned media obtained from previous retinal stem cell cultures, or from selected neural stem cell cultures, alone or in combination. This suggests an additional role in the control of human neuroretina-derived retinal stem cell (hNRSC) proliferation, for as yet uncharacterized autocrine factors, or co-factors.

When deriving stem cells from the human neural retina, it is necessary during dissection to manage the highly tenacious vitreous gel. This can be accomplished using a variety of techniques, alone or in combination, including vitrectomy, ocular inversion, mechanical resection and absorbent debridement, as well as enzymatic digestion. Suitable enzymes include, but are not limited to, hyaluronidases and collagenases. It is also particularly advantageous to remove all non-neural retinal tissue from the specimen used for retinal stem cell isolation. The non-neural tissue includes the optic nerve head and epithelium of the pars plana of the ciliary body, which is typically adherent along the peripheral margin (ora serrata).

The NRSC culture methods of the invention also differ from prior art techniques by initial exposure of cultured neuroretina-derived cells to serum (e.g. fetal calf serum), followed by complete change of the culture medium to a defined medium including specific growth factors. This technique has not been described in the context of stem cells derived from any layer of the retina or uveal tract, let alone the neuroretina. Initial mechanical dissociation of tissue through a sterile small pore filter screen allows one to minimize the use of enzymes that degrade cell surface molecules such as growth factor receptors.

Additionally, the in vitro derivation of cells from the neural retina is done with attention to the choice of antibiotics. Specifically, gentamicin is preferably not used in neural retinal cell cultures. Human NSRCs are advantageously cultured using a human protein as an optimal substrate for adhesion of human cells in the culture vessel, in this case fibronectin, overlying a base of polyornithine. Adherent cells are observed in the NRSC culture methods of the invention. Prior art methods described growing pigmented cells as non-adherent spheres.

The invention also encompasses the isolation of stem cells from the neuroretina of mice expressing the enhanced green fluorescent protein (eGFP) transgene and the transplantation of these cells to the brain and retina of non-transgenic recipients. The integration of these eGFP-expressing stem cells can be tracked in recipient animals.

BRIEF DESCRIPTION OF THE FIGURES

FIGS. 2A and 2B are photomicrographs of NRSCs in vitro, labeled with antibodies against retinal stem cell markers: Ki-67, expressed by mitotic cells (left, FIG. 2A) and nestin, an intermediate filament protein in neural stem cells and immature neurons (right, FIG. 2B).

FIGS. 5A and 5B are two exemplary in situ photomicrographs of "green", neuroretina-derived retinal stem cells (derived from GFP-expressing transgenic mice), 2 weeks after being grafted in a host adult rd-2 mouse eye, labeled with a red-labeled antibody specific for the photoreceptor-specific marker, rhodopsin.

FIGS. 6A-F are photomicrographs of "green" NRSCs grafted into various retinal sites, 2 weeks post-graft. FIGS. 6A-6C and FIGS. 6D-6F, respectively, show views of the same retinal site, under different illumination: GFP illumination (FIGS. 6A and 6D), red-labeled anti-rhodopsin antibodies (FIGS. 6B and 6E); and ordinary photomicrograph (FIGS. 6F).

FIGS. 9A and 9B are photomicrographs showing GFP (green, FIG. 9A) and rhodopsin (red, FIG. 9B) expression in RD-2 mouse vitreous, 2 weeks after grafting.

FIGS. 10A-10C are photomicrographs of the same graft site: retinal stem cells grafted to the subretinal space of adult retina "green" NRSC from transgenic GFP-expressing mice, grafted to the subretinal space of adult retina in lesioned B6 mouse subretinal space, 2 weeks after grafting. FIG. 10A shows GFP expression (green illumination); FIG. 10B shows recoverin expression (staining of cells with red-labeled anti-recoverin antibodies); and FIG. 10C shows an overlay or merged view of FIGS. 11A and 11B.

FIGS. 11A-11C are confocal micrographs of the same graft site: "green" NRSC from transgenic GFP-expressing mice, grafted to the subretinal space of adult retina in lesioned B6 mouse subretinal space, 2 weeks after grafting. FIG. 11A shows GFP expression (green illumination); FIG. 11B shows recoverin expression (staining of cells with red-labeled anti-recoverin antibodies); and FIG. 11C shows an overlay or merged view of FIGS. 11A and 11B.

FIGS. 12A-12C show confocal micrographs of the same graft site: "green" NRSC grafted into lesioned B6 mouse subretinal space, 4 weeks after grafting. FIG. 12A shows recoverin expression (staining of cells with red-labeled anti-recoverin antibodies); FIG. 12B shows GFP expression (green illumination); and FIG. 12C is an overlay or merged view of FIGS. 12A and 12B.

FIG. 19A shows the stem/progenitor cell before mitosis; FIG. 19B shows it during mitosis; and FIG. 19C shows it just after mitosis (with 2 daughter nuclei). FIG. 19C also shows a classic profile of an early, neural stem/progenitor cell.

DETAILED DESCRIPTION OF EMBODIMENTS

Figure 1A:
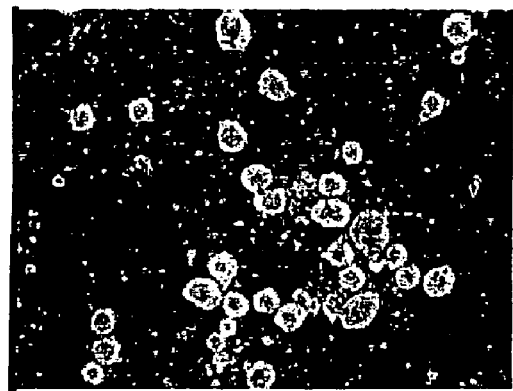
FIG. 1 depicts phase-contrast views (left, A) and green-fluorescent protein (GFP) illumination views (right, B) of GFP-expressing, neuroretina-derived retinal stem cell spheres at 3 days (top panel) and 6 days (bottom panel) after dissociation into single cell suspension.
Figure 1B:
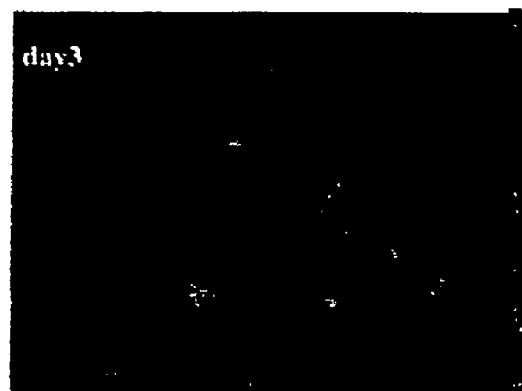
Figure 1C:
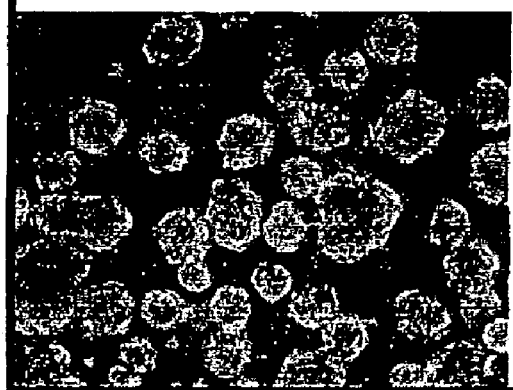
Figure 1D:
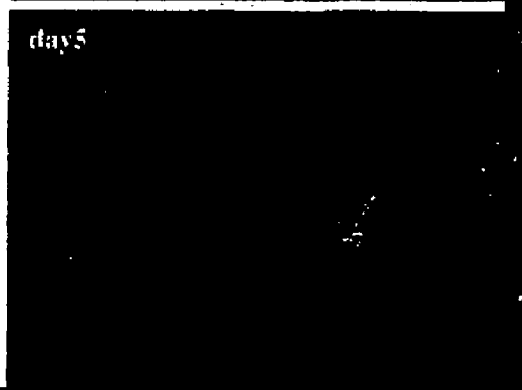

The invention relates to the isolation, characterization, and use of neuroretina-derived retinal stem cells (NRSC) and cell lines derived therefrom.

The NRSCs of the invention are isolated from neural retinal tissue from a donor mammal, such as a primate, rodent, domestic farm animal (e.g., human, mouse, rat, pig). Advantageously, the neural retinal tissue from which they are isolated should be substantially free of other non-neural, ocular tissue, including retinal pigmented epithelium.

The donor mammal can be an embryo, a neonate, or an adult. Surprisingly, the NRSCs can be isolated from neuroretinas of aged individuals. The NRSCs are capable of:
 a) self-renewal in vitro;
 b) differentiating into any one cell type of the group consisting of neurons, astrocytes, and oligodendrocytes;

c) integration into the neuroretina following transplantation to the posterior segment of the host eye; and
d) differentiation into photoreceptor cells when grafted onto a retinal explant, or into the mature eye of a recipient mammal.

We have found that the neuroretina-derived retinal stem cells of our invention express nestin (a marker of neural stem cells and immature neurons), and are non-pigmented (i.e., are not of retinal pigment epithelial origin). When cultured, these cells require the presence of at least one exogenous growth factor in a culture medium in order to proliferate in vitro. Effective exogenous growth factors include neurotrophins; mitogens; cytokines; growth factors; hormones; and combinations thereof, as will be appreciated by one of ordinary skill in the art. Advantageously, the NRSC-supportive culture medium includes one of the following factors or combinations of factors: epidermal growth factor (EGF), basic fibroblast growth factor (bFGF), a combination of bFGF and EGF, and a combination of EGF and bFGF and platelet-derived growth factor (PDGF).

The transplantation site or in situ environment of grafted NRSCs affect their differentiation and eventual phenotype. Differentiation of NRSCs into neurons has been confirmed by their expression of neuron-specific markers such as the neurofilament protein, NF-200. Differentiation of NRSCs into astrocytes has been demonstrated by expression of glial fibrillary acidic protein, GFAP. When grafted onto a retinal explant, or into the retina of a mature eye, the NRSCs have been found to integrate appropriately into the host architecture (e.g., outer nuclear layer), and to express rhodopsin, recoverin, or both, which proteins are markers for a mature photoreceptor phenotype. Thus the NRSCs provide a viable means of repopulating, and restoring photoreceptor function in, a dysfunctional retina. Such dysfunction includes, but is not limited to, disease, injury, and developmental defect.

The invention also encompasses a method of isolating and culturing retinal stem cells from a neuroretina of a donor mammal, comprising the following steps:

Step (a): A neuroretinal tissue is isolated from a donor eye, from an embryo, a neonate, or an adult donor mammal. The isolated neuroretinal tissue is preferably substantially free of vitreous humor or gel, optic nerve head tissue, pars plana epithelial tissue, and retinal pigmented epithelial tissue. It is preferably handled using aseptic technique.

Step (b): The isolated neuroretinal tissue is then mechnically masserated, and passed through a nylon mesh screen of about 100 micron pore size to dissociate the isolated neuroretinal tissue into cells.

Step (c): An aliquot of cells from step (b) is placed in a culture vessel, such as a plastic tissue culture flask, which is preferably coated with a protein layer. The protein layer is preferably of the same mammalian origin as the donor tissue from which the NRSCs are isolated. Advantageously, the layer may be polyornithine overlaid with laminin or fibronectin.

Step (d): The aliquot of cells is first incubated in an amount of a first cell culture medium to provide a cell concentration within a range of about $10^7$-$10^8$ cells/ml, for about 24 hours at about 35-39° C., and in an approximately 4-6% $CO_2$ atmosphere. The first cell culture medium includes a physiologically balanced salt solution containing a D-glucose content of about 0.5-3.0 mg/liter, preferably about 1 mg/liter, N2 Supplement, and about 5-15% fetal calf serum, as well as 5-15% by volume neural/retinal-conditioned media and an effective amount of at least one antibiotic (excluding gentamicin).

Step (e): After about 24 hours incubation in the first culture medium, that medium is removed from the culture vessel.

Step (f): Then, a second culture medium that is essentially serum-free, as well as gentamycin-free, is added to the culture vessel. The second culture medium includes a physiologically balanced salt solution containing a glucose content of about 0.5-3.0 mg.liter, preferably 1 mg/liter (e.g., DMEM/F-12 high glucose), N2 Supplement, at least one growth factor at a concentration of about 30-50 ng/ml per growth factor, an effective amount of L-glutamine (about 0.5-3 mM, preferably about 1 mM), an effective amount of neural progenitor cell-conditioned medium, and an effective amount of at least one antibiotic (excluding gentamicin), such as penicillin and/or streptomycin. Advantageously, penicillin and/or streptomycin may be added as follows: 10,000 units/ml pen, 10,000 microgram/ml strep, added 1:50-150, preferably 1:100, for a final concentration of 100 units/ml, 100 microgram/ml, respectively, in the culture medium. Those of ordinary skill in the art reading this specification will appreciate minor modifications that can be made to either of the culture media, without substantially altering their ability to support maintenance and growth of the NRSCs.

The isolation and culture method of the invention preferably further includes, in addition to step (f), regularly removing non-viable cells and a portion of the second culture medium from the culture vessel in which the NRSCs are cultured, and replacing said portion with an equivalent amount of fresh, second culture medium. This culture maintenance step may be performed approximately every 2-7 days during the lifetime of the NRSC culture.

The invention, by enabling long-term culture of neuroretina-derived retinal stem cells, also provides for the clonal derivation of NRSCs.

The invention also encompasses NRSCs that express reporter genes such as green fluorescent protein (GFP), which enable one to track the migration and integration of such cells when transplanted into a host retina, whether as an explant (in vitro) or into a recipient mammal (in vivo). GFP-expressing or "green" NRSCs can be isolated from transgenic animals expressing the enhanced GFP (eGFP) transgene product in all nucleated somatic cells. Alternatively, "green" NRSCs can be produced by secondarily inserting a GFP transgene into a clonally derived NRSC line. The GFP expressed by the NRSCs do not appear to have any adverse effect on normal development and functioning of these cells into full differentiated retinal cells or other neuronal cells.

The NRSCs provide means to study and to treat various ocular diseases, disorders, and injuries, particularly those involving retinal and neural retinal tissue.

The invention is further described with the following, non-limiting, examples.

EXAMPLE 1

Isolation of Retinal Stem Cells from Late Embryonic/Early Post Natal Mice and from Adult Mice Neural retinas were surgically removed from embryonic and postnatal transgenic mice expressing green fluorescent protein (Tgn(beta-act-EGFP)01Obsd to 05Obs) and immediately placed in PBS containing 3×antibiotics (penicillin/streptomycin). Neuroretinal tissue was finely minced using double scalpels, washed in PBS, collected into a 50 ml centrifuge tube and centrifuged at 1200 rpm for five minutes at 4C. The supernatant was removed and discarded after which time the pellet was resuspended in 5 ml of a 0.1% collagenase solution (Type 1) and immediately transferred to a sterile cup containing a magnetic stir bar. The neuroretinal tissue was gently stirred for 20 minutes then removed from the stir plate and tilted so that the undigested tissue would go to the bottom of the receptacle. The supernatant containing liberated cells was collected and forced through a 100 micron nylon mesh into a 50 ml centrifuge tube and centrifuged as before (1200 rpm etc.). The supernatant again was removed and discarded and the resulting cell pellet was resuspended into DMEM/Ham's F12 medium without fetal calf serum supplemented with EGF (40 ng/ml). Cells were seeded into 6 well plates and incubated at 37° C. in a humidified atmosphere consisting of 95% air: 5% carbon dioxide. The remaining tissue was subjected to several of these cycles until it was completely digested.

Cells were refed every 2 days with the medium described above in the following manner. Approximately 0.5 ml of medium was removed from a particular well and placed into a new well of a 6 well plate. An equal amount (approximately 0.5 ml) of freshly prepared medium was added to both wells.

Cell spheres were seen within 24 hours post isolation and were non-adherent at this point. As the spheres continued to grow and multiply in number, they reached a point at which they all attached to the bottom of the culture vessel. (The point at which this event occurs is variable depending on the isolation, the age of the mice, etc.). At this point, cultures were still refed as described and cells continued to proliferate on the bottom of the dish assuming a morphology similar to that of differentiated cells. This pattern of growth would continue for several days (7-10). Suddenly the cells would begin to detach and form a single cell suspension which would result in the formation of new precursor spheres. This cycle appears to persist as long as the cells are re-fed on a regular basis.

EXAMPLE 2

Isolation of Neuroretina-Derived Retinal Stem Cell Line from Adult Human Retinal Tissue Human retinal stem/progenitor cells of the invention are obtained from the neural retina and do not produce melanin. These retinal stem cells are thus classified as non-pigmented cells, although they may be found in association with pigment granules shed by other, pigmented cells when grown in co-cultures.

We have isolated a novel retinal stem cell type from post-mortem human neuroretinal tissue, including juvenile as well as aged donors (6-78 years of age, male and female). These cells can be derived from ice-cooled, unfrozen neuroretinal tissue even when greater than 24 hours have elapsed between the donor's demise and the initiation of culturing of the donor's neuroretina-derived cells.

Methodology

The non-pigmented human neuroretina-derived stem cells of the invention can be harvested from surgical specimens, as well as from tissue donated post-mortem. The cells can be obtained both postnatally and prenatally, over a wide range of donor ages. The cells of this invention can be obtained, surprisingly, from the neural retina of adult, even elderly donors, including those of 70 years of age or more.

Human ocular tissue in the form of whole globes, poles (globes with corneas removed), or neural retinal specimens were obtained from human donors and kept on ice, preferably in substantially sterile conditions. Tissue was maintained in Dulbecco's Minimal Essential Medium F-12 (DMEM/F-12; Omega Scientific), on ice and placed in culture anywhere from 6 to 36 hours after donation.

The eyes were dissected using sterile technique, with fluid detachment of the retina. Ocular inversion was used to manage the unwieldy vitreous body. Retinal tissue was dissected free from all other ocular tissues (i.e., none of the optic nerve head and surround, pars plana, or retinal pigmented epithelium (RPE) was included). The retinal tissue was then minced, mechanically extruded through a fine screen, with or without enzymatic treatment. The dissociated retinal cells were seeded into plastic, multi-welled plates or plastic tissue flasks (e.g., 6-well plates or T-25 flasks, Greiner), coated with a human protein layer (e.g., laminin or fibronectin) as an optimal substrate for adhesion of the human retinal cells. Particularly advantageous is the use of a coating of human fibronectin over polyornithine. Cells were initially suspended at high density in a medium containing Dulbecco's Minimal Essential Medium F-12 (DMEM/F-12) with high glucose (about 0.5-3.0 mg/liter, preferably about 1 mg/liter), serum (5-15%, preferably about 10% fetal calf serum (FCS)), and neural stem cell-conditioned medium in an incubator at about 37° C. and 5% carbon dioxide ($CO_2$) atmosphere. It was found advantageous to incubate the cells in the FCS-containing medium for about 24 hours. After 24 hours, the culture media was completely changed. At this time point, and later during culture, the composition of the culture medium was changed to a defined, serum-free media containing DMEM/F-12 high glucose medium, as well as neural stem cell-conditioned medium (5-15% by volume) N2 Supplement (Life Technologies), a relatively low concentration of L-glutamine (0.5-3 mM), and one or more growth factor(s) at high concentration (either EGF, bFGF, bFGF/EGF, or EGF/bFGF/PDGF; 20-50 ng/ml, preferably 40 ng/ml each, Promega), as well as penicillin and streptomycin. Gentamicin should not be used.

Subsequently, it was advantageous to perform, at least every 2-7 days, fractional exchange of culture medium with fresh, serum-free, gentamicin-free culture medium media, and removal of non-viable cells from the suspension. In some cases, it may be advantageous to perform such partial media exchange more frequently, as often as every 5 hours, for 3-7 days.

Viable adherent cells were readily identified within 1-3 days in culture. These non-pigmented cells were elongated in one axis, and frequently of fusiform or pod-like morphology. At the 7-day time point, adherent cells were typically larger and more numerous. Some were bipolar, others multipolar, and some extended long, thin processes. Over the second week, adherent cells continued to increase in number. Increases were highest in focal patches. Cells in these patches were frequently associated with additional rounded profiles that appeared to be budding off from their somata, typically distal to their nucleated center. Similar behavior is seen with both a brain-derived human neural progenitor line as well as the mouse-derived retinal stem cell line described in this invention. In other cases, the rounded profiles within a patch were seen to be floating in suspension or adherent and free standing, i.e., not juxtaposed to an elongated mother cell, thereby suggesting one mode by which these cells spread out in culture. In either case, the rounded profiles were visualized at various stages of mitosis, a process that could be observed to completion. Smaller rounded cells were also present in clusters covering the somata of underlying adherent cells, or rising up from them to form neurospheres. At the 18-day time point, the adherent population continued to increase in number and phenotypic complexity. Networks of long, thin neurite-like processes could be seen stretching between cells in an apparently directed manner, consistent with a neuronal phenotype. FIGS. 13-19 show various photomicrographs of non-pigmented retinal stem/progenitor cells derived from post-mortem neural retina of a normal adult human.

EXAMPLE 3

Preparation of Single-Cell, Adherent, Neuroretin-Aderived Retinal Stem Cells

Single-cell, adherent preparations of neuroretina-derived retinal stem cells (NRSC) may be prepared in the following manner, from a NRSC sphere culture. The single-cell preparations can be used to grow new NRSC cultures or be frozen for later use.

1. Begin with a neuroretina-derived retinal stem cell (NRSC) sphere culture, grown in EGF-containing media in a culture flask, e.g., T-75 (Corning), as previously described in the earlier.
2. Dissociate the cells by bathing them in a trypsin/EDTA solution: e.g., add about 2 ml of a 0.05% trypsin, 0.53 mM EDTA, 10×solution to the T-75 flask.
3. Break up the NRSC spheres by trituration with a flamed polished Pasteur pipette, of medium diameter (300-600 microns DIMENSIONS?), followed by trituration with a small tip diameter (DIMENSIONS 100-300 microns). Perform 10 triturations per tip size.
4. Add 10 mls $Ca^{2+}$ and $Mg^{2+}$-free HBSS to rinse.
5. Centrifuge at about 1100 rpm for about 3 min, and remove the supernatant.
6. Break up the remaining cell pellet by trituration with flamed polished pasteur pipettes, as before (step 3).
7. Respuspend the cells in approximately 10 ml $Ca^{2+}$- and $Mg^{2+}$-free Hanks' Balanced Salt Solution (HBSS) to rinse the cells, and centrifuge again as before. Remove all of the supernatant, resuspend the cells in about 1 ml fresh HBSS.
8. Break up the remaining cell pellet by trituration with briefly flamed, polished Pasteur pipettes as before (step 3).
9. Place the resulting cell suspension, at 1-9 million cells/ml, into protein-coated culture vessels, preferably laminin-coated flasks. Cells grow as single adherent cells, and reach confluence at about day 5 in epidermal growth factor-containing media (EGF media).

Freezing of Single Cell Adherent Retinal Stem Cell Cultures

Advantageously, neuroretina-derived retinal stem cells of the present invention, particularly those prepared as single-cell adherent stem cell cultures, may be frozen for long-term storage, at temperatures down to, e.g., –150° C. The frozen NRSC can be stored for at least 1 year without significantly affecting those NRSCs' viability, once thawed for culture and other use (cell viability upon thaw is greater than 95%). The NRSCs may be frozen as follows:

1. Begin with confluent neuroretina-derived retinal stem cell (NRSC) adherent cultures, grown in a culture flask such as T-75. Remove the culture medium.
2. Detach the cells from the culture flask (e.g., a plastic T-75 flask), by adding about 1-3 milliliters (ml), preferably 2 ml, of a trypsin/EDTA solution (preferably 0.05% trypsin, 0.53 mM EDTA, 10× solution). Let sit for about 1-5 minutes with agitation, preferably about 1 minute.
3. Add approximately 10 ml of $Ca^{2+}$ and $Mg^{2+}$ free Hanks Balanced Salt Solution (HBSS) to rinse out the trypsin/EDTA solution.
4. Centrifuge the flask at 1100 rpm for 3 minutes (min), and remove the supernatant from the flask.
5. Break up the remaining cell pellet by trituration with a briefly flamed, polished Pasteur pipette of medium tip diameter followed by one of small tip diameter. Perform 10 triturations per tip size.
6. Resuspend the cells in about 1 ml of 50% EGF media/50% Conditioned medium in an ampule (VWR), to which is added 75 microliters of dimethyl sulfoxide (DMSO). "Conditioned medium" is EGF medium that has been "conditioned" by neural stem cells, i.e. fed to such cells in culture, then removed and filtered. The medium contains various cell secretory products and some waste products. ("Neuroprogenitor cell-conditioned medium" is synonomous in this case with "conditioned medium".) "N-2 Supplement" is a proprietary neuronal survival supplement, available from GIBCO/life Science Tech., which is known to include tranferrin, insulin, and various growth factors. One of ordinary skill in the art understands that media with N-2 can be called "defined media", or "serum free media", to be distinguished from "serum containing media"
7. Place the ampule of resuspended cells in a Nalgene isopropyl freezing apparatus and place in a –80° C. freezer for at least 4 hours.
8. Move the ampule to a –150° C. freezer for long-term storage.

Thawing Frozen NRSC for Re-Use

One may thaw frozen, single-cell adherent NRSC samples according to the following, preferred method:

1. Thaw the vial or ampule of frozen NRSCs in an approximately 37° C. degree water bath.
2. Transfer the cells to 15 ml tubes in 10 mls ice-cold EGF media (at a cell concentration of about $1-9\times10^6$ cells/ml.
3. Centrifuge the resuspended cells at about 800 rpm for about 3 minutes.
4. Remove the supernatant, resuspend the NRSC cells in 1 ml EGF medium, and place them into a T-75 flask.

Characterization of Retinal Stem Cells

Weiss et al.[8] has set forth five characteristics of stem cells, in terms of the ability to: (1) proliferate; (2) self-maintain or self-renew, with self-renewal occurring by symmetric division; (3) generate a large number of progeny; (4) retain, over time, pluripotency, the ability to differentiate into a variety of cell lineages; and (5) generate new cells in response to disease or injury. We have characterized the neuroretina-derived retinal stem cells that we have isolated, in vivo and in vitro, and have determined them to be true retinal stem cells based upon the following evidence:

Proliferation and Self-Renewal (criteria (1)-(3)): Under high EGF (40 ng/ml) conditions, the cells form spheres that label with Ki-67, express nestin, and form new spheres when dissociated into single cells. This has been demonstrated for at least 5 months in vitro.

Pluripotency (Criterion (4)): Upon treatment with 10% serum, these cells differentiate into all three neuronal lineages: neurons (NF-200 and MAP-2 expression) astrocytes (GFAP expression) and oligodendrocytes (GalC).

Integration Following Transplantation Into The Retina (Criteria (4) and (5)): We have found that the cells can integrate with host retina following in vivo grafting or explanting to a diseased retina (see, e.g., FIGS. 6-12).

Retina Specific Differentiation (Criteria (4)-(5)): A hallmark of retinal lineage is the expression of retinal specific markers. Unlike any previously described stem cells, these cells are capable of differentiating into photoreceptors when transplanted to the mature diseased eye. This is demonstrated by the grafted NRSCs expressing rhodopsin (see, e.g., FIGS. 5, 6, 9, 10), and recoverin (see, e.g., FIGS. 7, 8, 11, 12) in situ.

Discussion of Experimental Results

Our experimental results are discussed with reference to the figures.

FIG. 1 depicts phase contrast (left, FIG. 1A) and GFP illumination (right, FIG. 1B) views of neuroretinal stem cell spheres 3 (top) and 6 days (bottom) after dissociation into single cell suspension. This panel shows high and consistent expression of GFP marker (green), and progressive and rapid growth of spheres from single cells.

FIG. 2 depicts expression of stem cell markers by neuroretinal stem cells in vitro. Spheres show high number of cells staining with Ki-67, a marker for cells undergoing mitosis (left, A). These spheres also express nestin, an intermediate filament protein seen in neural stem cells and immature neurons (right, B).

Figure 3B:
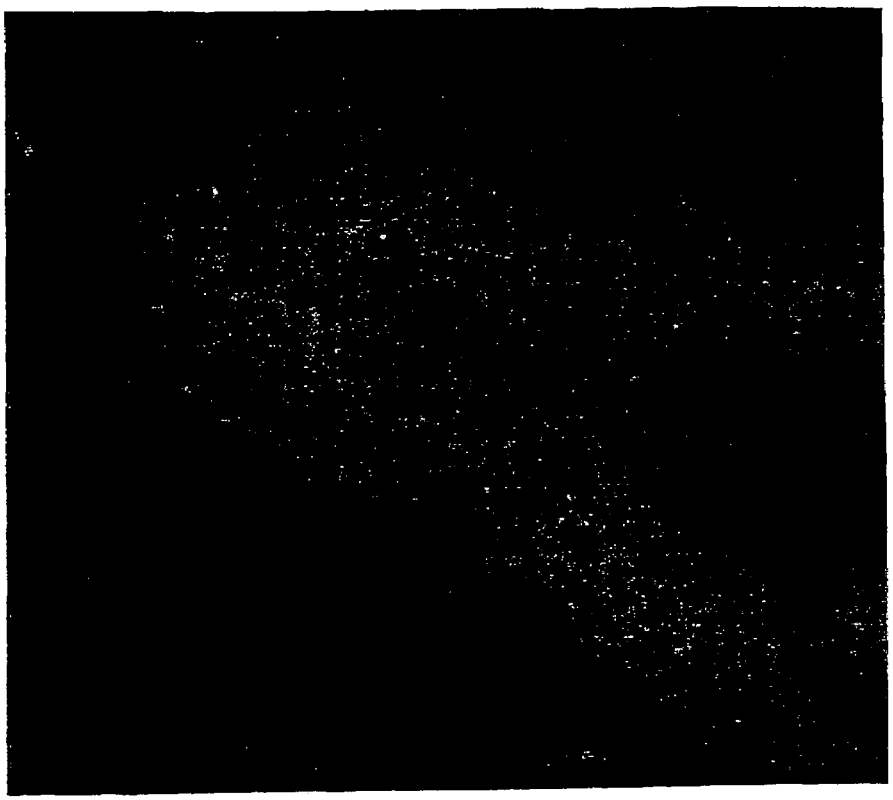
FIGS. 3A and 3B are photomicrographs of neuroretina-derived stem cells after their in vitro exposure to serum, labeled with an antibody against glial fibrillary acidic protein, a marker for astrocytes (anti-GFAP, left, FIG. 3A) and an antibody against neurofilament of 200 kD, a marker for mature neurons (anti-NF200; right, FIG. 3B).
Figure 3A:
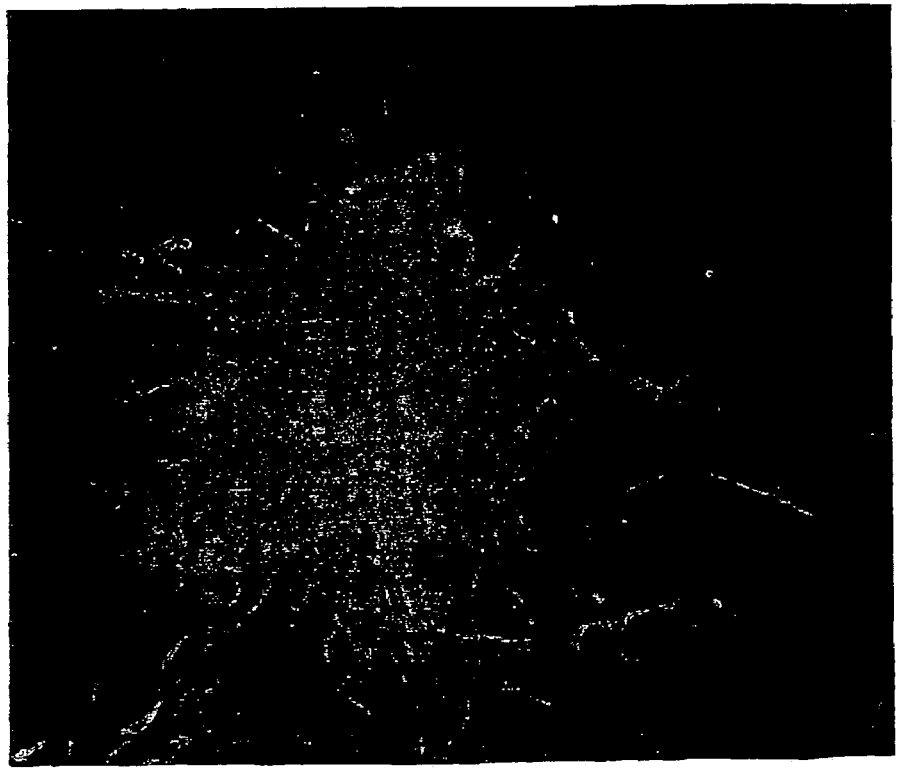
Figure 4A:
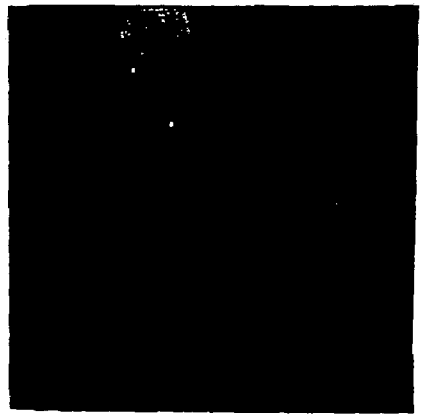
FIGS. 4A-4D are green fluorescent protein(GFP)-illuminated photomicrographs of four examples of mouse retinal explant recipient tissue (obtained postnatally on day 1), co-cultured with mouse retinal stem cell spheres for 7 days in vitro.
Figure 4B:
Figure 4C:
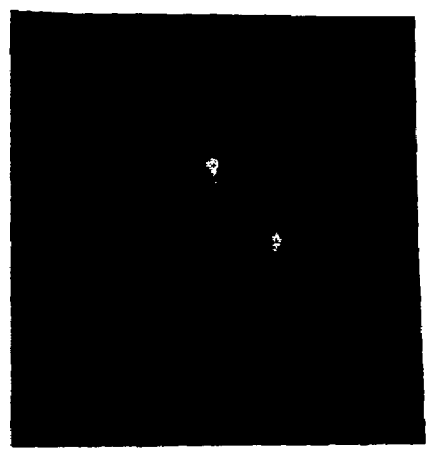
Figure 4D:
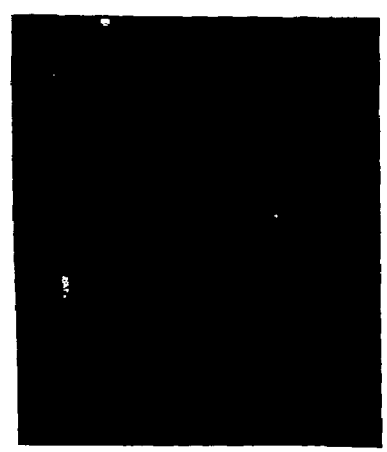

As can be seen from FIG. 3, upon exposure to serum (e.g., 10% fetal calf serum), and withdrawal of EGF, retinal stem cell spheres of the invention adhere to the substrate (e.g., laminin), and undergo neuronal and astrocytic differentiation. This is indicated by expression of GFAP (left, A; glial fibrillary acidic protein, a marker for astrocytes) and NF-200 (right, B; neurofilament, 200 Kd, a marker for mature neurons).

FIG. 4) Four examples of day 1 postnatal retinal explant recipient tissue co-cultured with retinal stem cell spheres for 7 days in vitro. Over the 7 days, the GFP positive cells (green) have migrated into the retina, assumed neuronal configurations, and elaborated processes into the host retina.

FIG. 5) Two examples of the expression of the photoreceptor specific marker rhodopsin (red-labeled with anti-rhodopsin) by retinal stem cells grafted to the adult rd-2 mouse eye. Here, 2 weeks after grafting, two cells can be seen expressing high levels of rhodopsin, as well as developing photoreceptor morphology.

Figure 7:
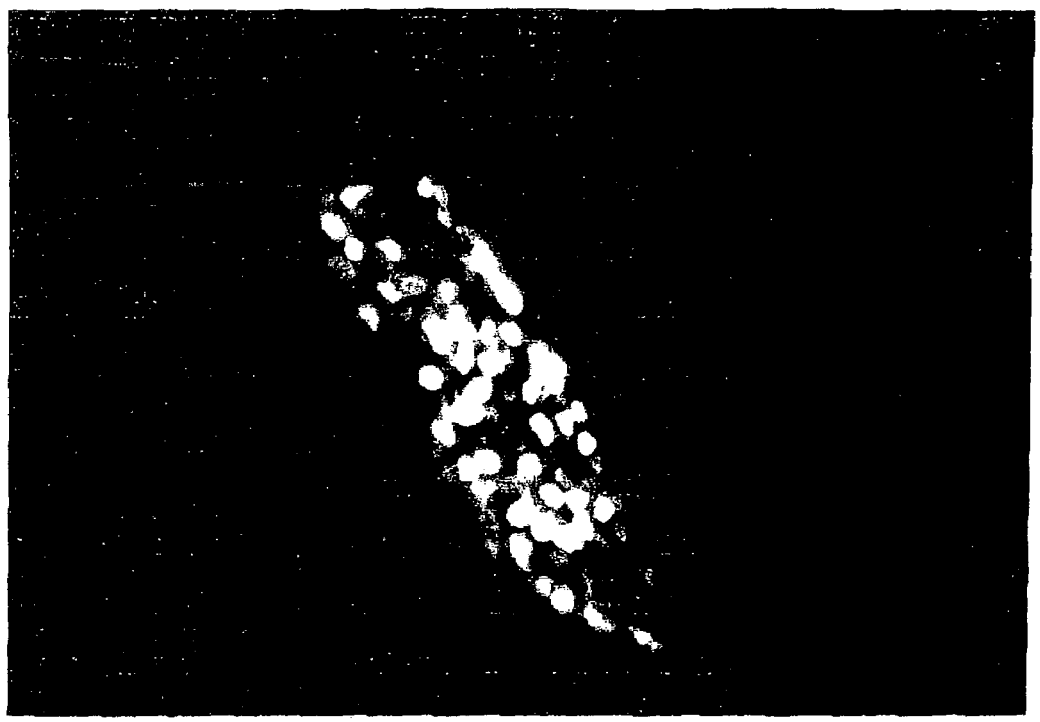
FIG. 7 is a confocal photomicrograph of "green" NRSCs grafted into an extra-ocular site, 2 weeks post-graft, labelled with red-labeled, anti-recoverin antibodies.
Figure 8:
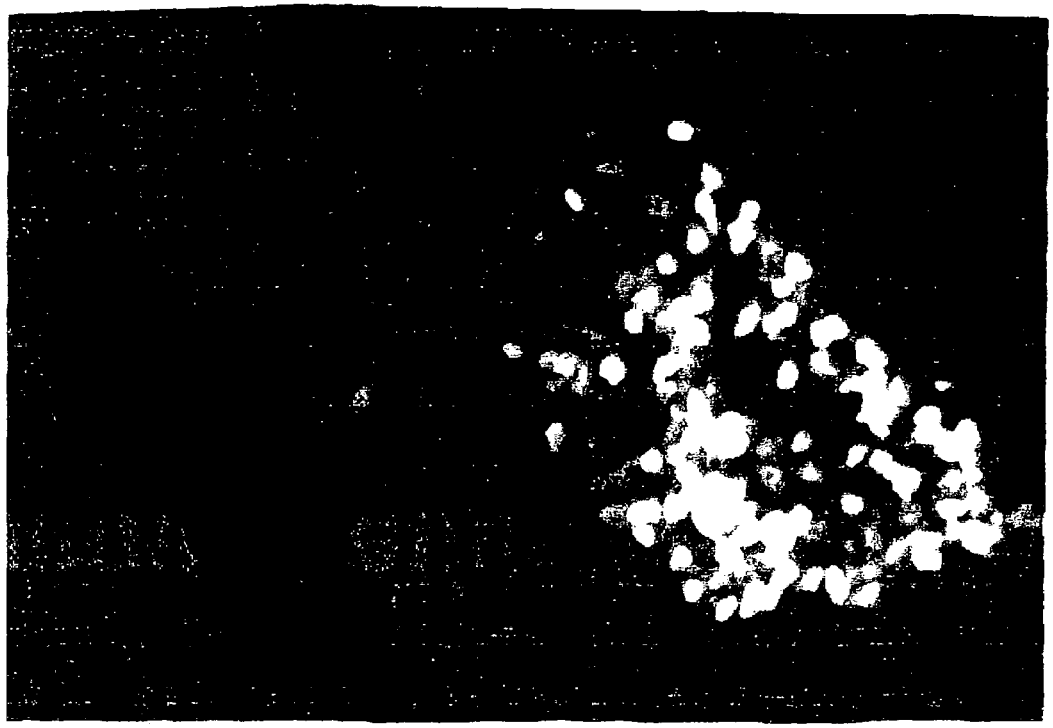
FIG. 8 is a confocal photomicrograph of "green" NRSCs grafted into a retinal site, 2 weeks post-graft, labelled with anti-recoverin antibodies.

FIGS. 6-8 show the influence of graft environment: grafting the NRSC into retinal sites promotes the cells' differentiation into retinal cells, including photoreceptor cells (i.e., cells expressing rhodopsin and recoverin, known markers of mature photoreceptors). FIG. 6 shows that neuroretina-derived retinal stem cells grafted into a retinal site can express rhodopsin in situ. FIG. 7 shows that NRSCs grafted into an extraocular environment, can express recoverin by grafted retinal stem cells n situ. FIG. 8 shows expression of recoverin by NRSCs grafted into a retinal environment.

FIGS. 9-12 show that NRSCs can integrate into the adult retina, even in diseased or lesioned retinal sites of adult recipient mammals into which the NRSC are grafted.

FIGS. 9A-B depict photomicrographs showing GFP (green) and rhodopsin (red) expression in RD-2 mouse vitreous, 2 weeks after grafting. Neuro-derived retinal stem cells grafted to the vitreous of adult diseased retina can express rhodopsin.

The photomicrographs of FIGS. 10A-10C show that mouse, GFP-expressing NRSC grafted to the subretinal space of a lesioned, adult retina in a B6 mouse, also express recoverin in lesioned B6 mouse subretinal space, 2 weeks after grafting. FIG. 10A shows GFP expression (green); FIG. 10B shows recoverin expression (red); and FIG. 10C shows an overlay or merged view of FIGS. 10A and 10B (yellow indicating the co-expression of GFP and recoverin by the grafted RSCs).

FIGS. 11A-C and 12A-C depict photomicrographs of "green", mouse neuroretina-derived retinal stem cells transplanted to a host adult retina (e.g., lesioned B6 mouse), and the sites of their integration. These green neuroretina-derived RSCs, isolated from transgenic GFP-expressing mice, form self-renewing neurospheres and show uniform green fluorescence under FITC illumination and thus are easily identified after transplantation to the adult mouse retina (FIGS. 11A-11C and 12A-12C). NRSC grafted into the subretinal space of adult retina can express recoverin (FIGS. 11A-11C). Recoverin and GFP co-expression are seen in the outer nuclear layer of mechanically injured or lesioned B6 mouse retina (FIGS. 12A-12C), onto which is grafted the neuroretina-derived RSC of the invention. This proves that the NRSC differentiate into cells of retinal lineage, when grafted to dystrophic adult mouse retina.

FIGS. 13-19 are photomicrographs of human NRSCs of the invention, in culture. These cells were able to proliferate in vitro, when cultured according to the methods of the invention. Upon long-term exposure to fetal calf serum, these hNRSCs can differentiate into various neuronal cells.

Figure 13:
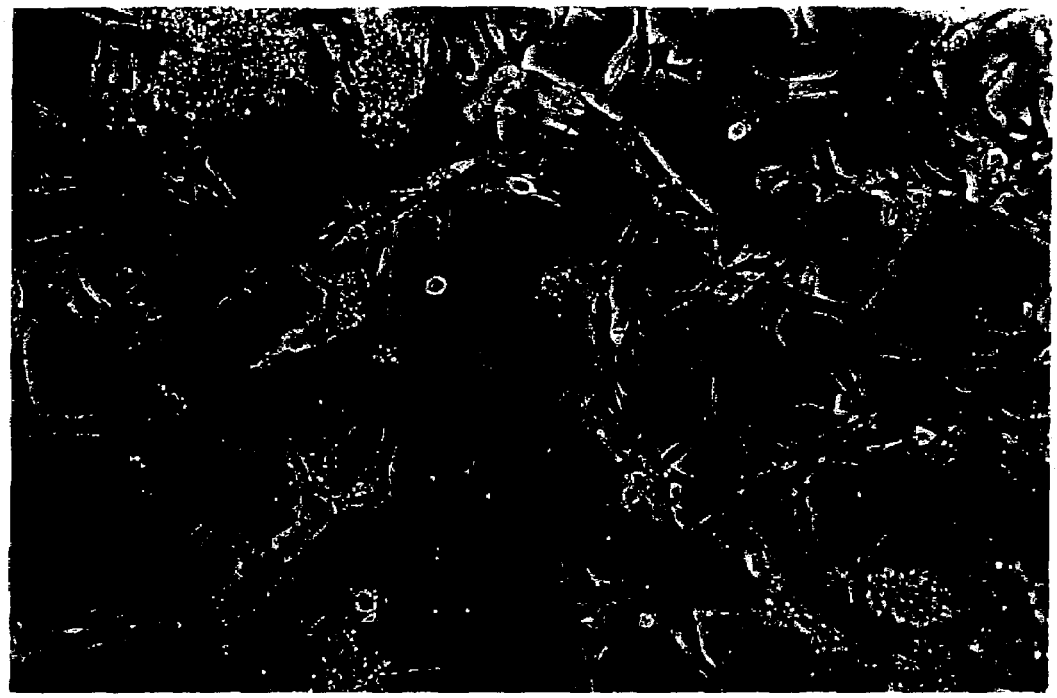
FIG. 13 a low-power photomicrograph of cultured, human neuroretina-derived stem cells (hNRSCs), showing bipolar, multipolar, and round cells, with neuritic processes.

FIG. 13 is a low-power photomicrograph of cultured, human neuroretina-derived stem cells (hNRSCs), showing bipolar, multipolar, and round cells, with neuritic processes.

Figure 14:
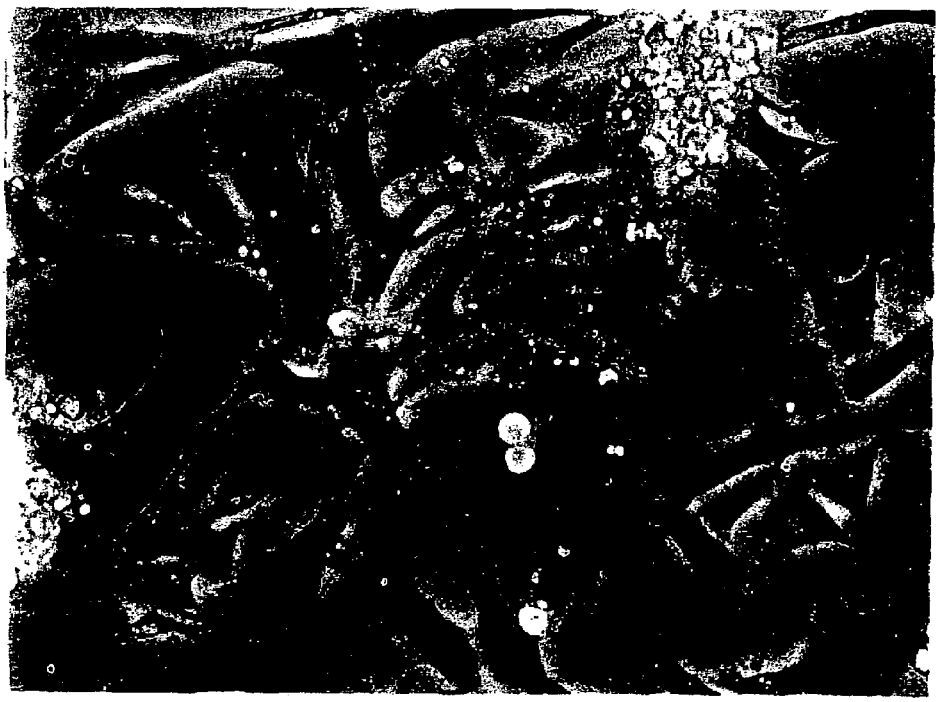
FIG. 14 is a photomicrograph of hNRSCs undergoing cell division.

FIG. 14 is a photomicrograph of hNRSCs undergoing cell division.

Figure 15:
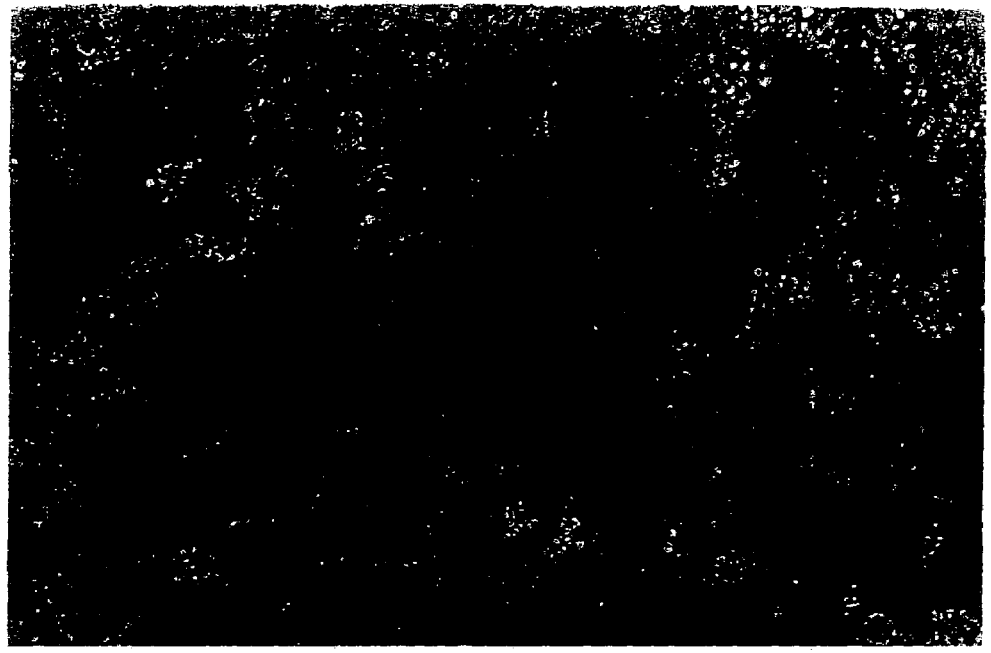
FIG. 15 is a low-power photomicrograph of cultured hNR-SCs, showing dividing cells and progenitor cells. The cells are observed in another sequence to be non-pigmented.

FIG. 15 is a low-power photomicrograph of cultured hNRSCs, showing dividing cells and progenitor cells. The cells are observed in another sequence to be non-pigmented.

Figure 16:
FIG. 16 is a low-power photomicrograph of cultured hNR-SCs, developing long neuritic processes.

FIG. 16 is a low-power photomicrograph of cultured hNRSCs, developing long neuritic processes.

Figure 17:
FIG. 17 is a phase photomicrograph showing the mitotic profile of hNRSCs.

FIG. 17 is a phase photomicrograph showing the mitotic profile of cultured hNRSCs.

Figure 18:
FIG. 18 is a bright-field photomicrograph of hNRSCs, showing that they are not pigmented.

FIG. 18 is a bright-field photomicrograph of hNRSCs, showing that they are not pigmented.

Figure 19A:
FIGS. 19A-19C are sequentially timed photomicrographs of the same cultured hNRSC specimen, showing a retinal stem or progenitor cell undergoing cell division.
Figure 19B:
Figure 19C:

FIGS. 19A-19C are sequentially timed photomicrographs of the same cultured hNRSC specimen, showing a retinal stem or progenitor cell undergoing cell division. FIG. 19A shows the stem/progenitor cell before mitosis; FIG. 19B shows it during mitosis; and FIG. 19C shows it just after mitosis (with 2 daughter nuclei). FIG. 19C also shows a classic profile of an early, neural stem/progenitor cell.

Uses

The neuroretina-derived retinal stem cells of the invention may be used for studying development of the retina and eye, as well as factors affecting such development, whether beneficially or adversely. This application is possible in part by means of enhanced green fluorescent protein-expressing NRSC, such as those derived from a transgenic donor mammal. They allow tracking, in vivo, of the migration, integration, and development of neuroretina-derived retinal stem cells that are transplanted into a host recipient.

The neuroretina-derived retinal stem cells of the invention may be useful for transplantation into a mammalian recipient suffering from dysfunctions of the eye. They may be used advantageously to repopulate or to rescue a dystrophic ocular tissue, particularly a dysfunctional retina. Retinal dysfunction encompasses any lack or loss of normal retinal function, whether due to disease, mechanical or chemical injury, or a degenerative or pathological process involving the recipient's retina. The NRSCs may be injected or otherwise placed in a retinal site, the subretinal space, vitreal cavity, or the optic nerve, according to techniques known in the art. This includes the use of a biodegradable substrates as a carrier for the RSCs.

Advantageously, as supported by the rhodopsin and recoverin expression data presented before, the NRSCs of the invention may be used to compensate for a lack or diminution of photoreceptor cell function. Examples of retinal dysfunction that can be treated by the retinal stem cell populations and methods of the invention include but are not limited to: photoreceptor degeneration (as occurs in, e.g., retinitis pigmentosa, cone dystrophies, cone-rod and/or rod-cone dystrophies, and macular degeneration); retina detachment and retinal trauma; photic lesions caused by laser or sunlight; a macular hole; a macular edema; night blindness and color blindness; ischemic retinopathy as caused by diabetes or vascular occlusion; retinopathy due to prematurity/premature birth; infectious conditions, such as, e.g., CMV retinitis and toxoplasmosis; inflammatory conditions, such as the uveitidies; tumors, such as retinoblastoma and ocular melanoma; and for replacement of inner retinal neurons, which are affected in ocular neuropathies including glaucoma, traumatic optic neuropathy, and radiation optic neuropathy and retinopathy.

Other examples of retinal dysfunction that can be treated by use of the stem cells and method of the invention are well-known to one of ordinary skill in the art, and may be found in, e.g., van der Kooy et al., U.S. Pat. No. 6,117,675 (issued September 2000), or PCT International Application No. PCT/US00/03534, which relates to integration of transplanted neural progenitor cells of non-retinal origin, into neural tissue of immature dystrophic recipients. The teachings of those documents are entirely incorporated herein by reference. Of particular significance are their teachings relating to neuronal stem cells, retinal disease and other dysfunction, and culture and uses of stem cells generally.

In using the NRSCs to treat retinal dysfunction, one may, in conjunction with introducing the NRSCs into a recipient's eye, administer a substance that stimulates differentiation of the neuroretina-derived stem cells into photoreceptors cells or other retinal cell types (e.g., bipolar cells, ganglion cells, horizontal cells, amacrine cells, Mueller cells). When NRSCs are introduced to treat a neural dysfunction of the eye, one may also utilize a substance (or combination of substances) that stimulates differentiation of the neuroretina-derived stem cells into neurons, astrocytes, or oligodendrocytes.

The cells of this invention demonstrate constitutive expression of a reporter transgene (GFP). They can also be modified to express other genes of interest, including therapeutic gene products, constitutively or in an inducible manner.

The treatment methods of the invention are directed at mammalian recipients, whether immature or mature/adult, including humans, mice, rats, or domesticated animals that suffer from some ocular, particularly retinal, dysfunction. The NRSC donor and recipient may be of the same or different species. Examples of cross-species donor and recipient pairs include the following pairs: a rat donor and a mouse recipient; a mouse donor and a rat recipient; a pig donor and a human recipient. The donor and the recipient may be allogeneic or syngeneic.

From the foregoing, it will be appreciated that, although specific embodiments of the invention have been described herein for purposes of illustration, various modifications may be made without deviating from the spirit and scope of the invention as set forth in the appended claims.

As well, all publications, patents, and patent applications are herein incorporated by reference in their entirety to the same extent as if each individual publication, patent, or patent application was specifically and individually indicated to be incorporated by reference in its entirety.

REFERENCES

1. Reynolds, B. A., Weiss S. *Science* 255, 1701-1710 (1992).
2. Pittenger, M. F. et al. *Science* 284, 143-147 (1999).
3. Flax, J. D. et al. *Nat. Biotech.* 18, 1033-1039 (1998).
4. Young, M. J. et al. *Molec. Cell. Neurosci* 16, 1997-2005 (2000).
5. Yeh, E., Gustafson, K., Boulianne, G. L. *Proc. Natl. Acad. Sci. USA* 92, 7036-7040 (1995).
6. Amsterdam, A., Lin, S., Hopkins, N. *Dev. Biol.* 171, 123-129 (1995).
7. Okabe, M. et al. *FEBS Lett.* 407, 313-319 (1997).
8. Weiss et al. *TINS Review* 19(9):1-13 (1996).
9. van der Kooy, D. et al., U.S. Pat. No. 6,117,675 (2000).
10. Kelley M. W., Turner J. K., Reh T. A. . *Invest Ophthalmol Vis Sci.* 36(7):1280-9.; 1995.

What is claimed as the invention is:

1. A method of repopulating photoreceptor cells of a mammal, said method comprising the steps of:
   providing neuroretina-derived retinal stem cells obtained from a neurosphere from a mammalian donor; and
   introducing said neuroretina-derived retinal stem cells locally into a retinal site, a subretinal space, or a vitreal cavity of an eye of a mammalian recipient, wherein said donor mammal and said recipient mammal are allogeneic or syngeneic, and whereby said photoreceptor cells repopulate a mammalian retina.

2. The method of claim 1, wherein the neuroretinal-derived retinal stem cells are clonally derived.

3. The method of claim 1, wherein the mammal is a human.

4. The method of claim 1, wherein the donor and the recipient are allogeneic.

5. The method of claim 1, wherein the donor and recipient are syngeneic.

6. The method of claim 3, wherein the human recipient is a neonate.

7. The method of claim 3, wherein the human recipient is an adult.

* * * * *